United States Patent
Sauer et al.

(10) Patent No.: US 7,251,306 B2
(45) Date of Patent: Jul. 31, 2007

(54) METHODS, APPARATUS, AND SOFTWARE TO FACILITATE ITERATIVE RECONSTRUCTION OF IMAGES

(75) Inventors: Ken David Sauer, South Bend, IN (US); Jean-Baptiste Thibault, Milwaukee, WI (US); Charles Addison Bouman, West Lafayette, IN (US); Jiang Hsieh, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 214 days.

(21) Appl. No.: 10/991,177

(22) Filed: Nov. 17, 2004

(65) Prior Publication Data

US 2006/0104410 A1    May 18, 2006

(51) Int. Cl.
*H05G 1/60* (2006.01)
(52) U.S. Cl. .......................................... 378/4; 378/207
(58) Field of Classification Search ............. 378/4–21, 378/901, 98.11, 98.12, 207, 210
See application file for complete search history.

(56) References Cited

U.S. PATENT DOCUMENTS

| | | | | |
|---|---|---|---|---|
| 4,991,093 A | * | 2/1991 | Roberge et al. | 382/131 |
| 5,253,171 A | * | 10/1993 | Hsiao et al. | 378/4 |
| 6,002,738 A | * | 12/1999 | Cabral et al. | 378/4 |
| 6,002,739 A | * | 12/1999 | Heumann | 378/8 |
| 6,166,853 A | * | 12/2000 | Sapia et al. | 359/559 |
| 2003/0076988 A1 | * | 4/2003 | Liang et al. | 382/131 |
| 2003/0161443 A1 | * | 8/2003 | Xiao et al. | 378/210 |
| 2005/0078861 A1 | * | 4/2005 | Usikov | 382/131 |
| 2005/0105693 A1 | * | 5/2005 | Zhao et al. | 378/210 |
| 2006/0002504 A1 | * | 1/2006 | De Man et al. | 378/4 |
| 2006/0067461 A1 | * | 3/2006 | Yin et al. | 378/5 |
| 2006/0120579 A1 | * | 6/2006 | Skoglund et al. | 382/128 |

* cited by examiner

*Primary Examiner*—Courtney Thomas
*Assistant Examiner*—Alexander Taningco
(74) *Attorney, Agent, or Firm*—Armstrong Teasdale LLP

(57) ABSTRACT

A method of reconstructing an image includes performing an iterative CT X-ray image reconstruction using a model including a point spread function (PSF) to reconstruct an image.

23 Claims, 2 Drawing Sheets

METHODS, APPARATUS, AND SOFTWARE TO FACILITATE ITERATIVE RECONSTRUCTION OF IMAGES

BACKGROUND OF THE INVENTION

This invention relates generally to methods, apparatus, and software for reconstructions of images in computed tomography (CT), and more particularly to methods, apparatus, and software for iterative reconstruction techniques.

Image reconstruction from helical CT scan data benefits from the flexibility of iterative reconstruction techniques. Conventional filtered backprojection suffers from interpolation errors inherent in the approximation of in-plane measurements from helical scans. These problems become especially pronounced with multi-slice detector arrays. Iterative techniques rely on successive approximations of an image, with adjustments of image values based on the difference between measured data and simulated measurements from the candidate image. Let x be a vector containing a 3-D reconstruction of the object; the elements in x will be numbers representing X-ray densities of volumetric elements, called "voxels," in the three-dimensional object to be imaged. Furthermore, let y be the actual measurements, representing samples from what will subsequently be called the "sinogram," and let F(x) be the expected values of the sinogram when the 3-D cross section being reconstructed is assumed to be x. Importantly, the model F(x) includes the precise geometry of the helical scan pattern and the source/detector structure, so it can directly account for the helical scan measurements. The difference between the measurements y and their expected values is commonly referred to as "noise," and may be incorporated into the model in the equation y=F(x)+n, where n represents the noise vector. The optimization problem in iterative reconstruction may be expressed as $$\hat{x} = \underset{x}{\operatorname{argmin}} \left\{ \sum_{i=0}^{M} D_i(y_i, F_i(x)) + U(x) \right\} \quad (1)$$

F transforms an image x in a manner imitative of the CT system, y is the available sinogram data and the functional $D_i$ is a function which penalizes distance between measurement i and the corresponding simulated i-th forward projection of x. U(x) is a regularization term which penalizes local voxel differences. A common embodiment of (1) takes the form $$\hat{x} = \underset{x}{\operatorname{argmin}} \left\{ \sum_{i=0}^{M} w_i |y_i - F_i(x)|^2 + U(x) \right\}, \quad (2)$$

where $w_i$ is a constant which weights the contribution of measurement i to the objective function. Frequently, a linear model of the form $F(x)=Ax$ is used, linearizing the relation between x and y with a matrix A. At each iteration, the algorithm finds a perturbation of x which will decrease the value of the above expression. Following adjustment of x, new forward projections by the operator F allow calculation of directions for further improvements. The computation of these simulated forward projections extracts a high computational cost, since storage of the matrix (A) describing the mapping between the image and the sinogram remains infeasible in practical computing systems, and components of F must be recomputed and discarded at each iteration. The quality of the iterative reconstructions depends strongly on the degree to which the mapping mirrors physical reality in the CT scanner.

The basic operation for both forward and backprojection in iterative reconstruction is the computation of the effect of a single element in a digital three-dimensional image on the attenuation measurements of the sinogram. In a typical reconstruction, a given entry in the matrix A of Ax must be used twice as many times as there are iterations, and the number of non-zero entries is extremely large. Because voxels may be modeled as representing rectangular solids in three dimensions, the attenuation of voxel j on sinogram measurement i may be approximated by the length of the line segment between a source and a detector i lying within voxel j, as illustrated in FIG. 3. Such a computational model suffers from several limitations. First, the line-clipping algorithm commonly used to find the length of this line segment consumes the greatest share of iterative computation, saddling these methods with reconstruction times orders of magnitude larger than those of conventional methods. Second, the line segment length is but a coarse approximation of the effect of a volume element on a detector's radiation. The non-zero sizes of both detectors and X-ray source cause blurring of these effects and can limit resolution of reconstructed images. The two-dimensional dosage profile of the X-ray focal spot is often unknown even if its shape is fixed.

BRIEF DESCRIPTION OF THE INVENTION

In one aspect, a method of reconstructing a CT X-ray image is provided. The method includes performing an iterative image reconstruction using a model function including a point spread function (PSF) to reconstruct an image.

In another aspect, a computer readable medium is provided. The medium is encoded with a program configured to instruct a computer to generate a model function including a point spread function (PSF), and reconstruct an X-ray CT image using the model.

In yet another aspect, a Computed Tomography (CT) System is provided. The system includes an X-ray source, a radiation detector, and a computer coupled to the X-ray source and the radiation detector. The computer is configured to perform an iterative image reconstruction using a model function including a point spread function (PSF) to reconstruct an X-ray image.

DETAILED DESCRIPTION OF THE INVENTION

Figure 1:
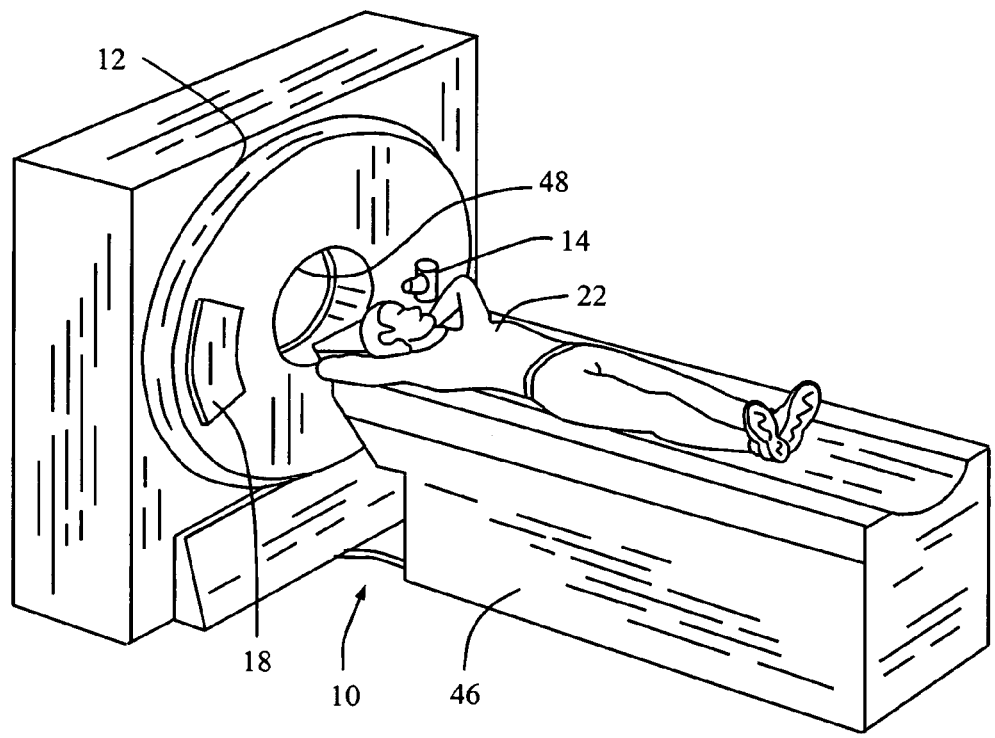
FIG. 1 is a pictorial view of a CT imaging system embodiment.

In some known CT imaging system configurations, a radiation source projects a beam which passes through an object being imaged, such as a patient. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In third generation CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view". A "scan" of the object includes a set of views made at different gantry angles, or view angles, during one revolution of the radiation source and detector.

In an axial scan, the projection data is processed to reconstruct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

To further improve the data acquisition, multi-slice or volumetric CT is built. Such a system collects multiple projections simultaneously by using a detector consisting of multiple detector rows. In such configuration, the fan beam geometry becomes a cone beam geometry.

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

Figure 2:
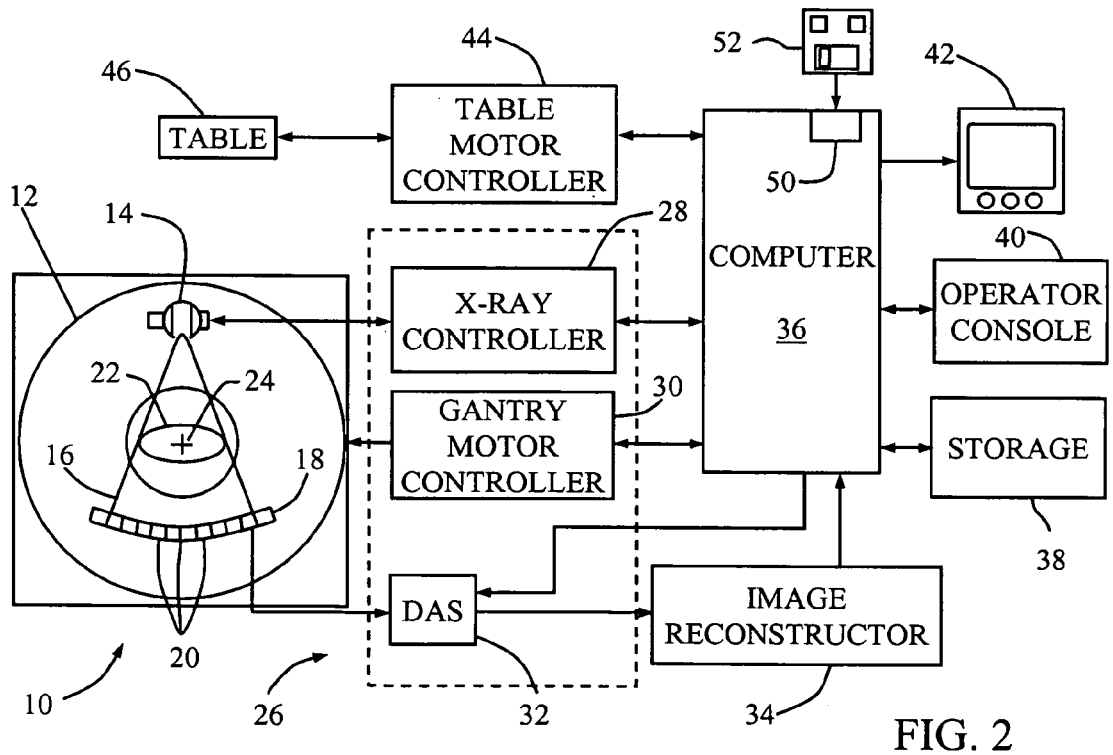
FIG. 2 is a block schematic diagram of the system illustrated in FIG. 1.

FIG. 1 is a pictorial view of a CT imaging system 10. FIG. 2 is a block schematic diagram of system 10 illustrated in FIG. 1. In the exemplary embodiment, a computed tomography (CT) imaging system 10, is shown as including a gantry 12 representative of a "third generation" CT imaging system. Gantry 12 has a radiation source 14 that projects a cone beam 16 of X-rays toward a detector array 18 on the opposite side of gantry 12.

Detector array 18 is formed by a plurality of detector rows (not shown) including a plurality of detector elements 20 which together sense the projected X-ray beams that pass through an object, such as a medical patient 22. Each detector element 20 produces an electrical signal that represents the intensity of an impinging radiation beam and hence the attenuation of the beam as it passes through object or patient 22. An imaging system 10 having a multislice detector 18 is capable of providing a plurality of images representative of a volume of object 22. Each image of the plurality of images corresponds to a separate "slice" of the volume. The "thickness" or aperture of the slice is dependent upon the thickness of the detector rows.

During a scan to acquire radiation projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of radiation source 14 are governed by a control mechanism 26 of CT system 10. Control mechanism 26 includes a radiation controller 28 that provides power and timing signals to radiation source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized radiation data from DAS 32 and performs high-speed image reconstruction. The reconstructed image is applied as an input to a computer 36 which stores the image in a storage device 38.

Computer 36 also receives commands and scanning parameters from an operator via console 40 that has a keyboard. An associated display 42 allows the operator to observe the reconstructed image and other data from computer 36. The operator supplied commands and parameters are used by computer 36 to provide control signals and information to DAS 32, radiation controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Generally, a processor in at least one of DAS 32, reconstructor 34, and computer 36 shown in FIG. 2 is programmed to execute the processes described below. Of course, the method is not limited to practice in CT system 10 and can be utilized in connection with many other types and variations of imaging systems. In one embodiment, computer 36 is programmed to perform functions described herein, and, as used herein, the term computer is not limited to just those integrated circuits referred to in the art as computers, but broadly refers to computers, processors, microcontrollers, microcomputers, programmable logic controllers, application specific integrated circuits, and other programmable circuits.

Herein described are methods, apparatus, and software that improve the accuracy of forward projection models in iterative CT image reconstruction by including a point spread function (PSF) in the model of the CT system. In any finite-dimensional description of the CT system's behavior, as in the function F above, there exists a mapping from a single entry in the image vector x to the data entries in the sinogram y. Physically, this may be thought of as the effect of a unit of attenuating mass at the location of voxel j on the measurement at detector i in the CT system. The PSF is a model of the deviation of the true values of these mappings from some geometrically ideal relation. This ideal may be, for example, the mapping of a point in the three dimensional image to a contribution to a single detector's value in the sinogram. Alternatively, the point in x may be modeled as a constant-valued cube of material centered at the physical location of the point, and the mapping as the length of the intersection between the cube and a line from the X-ray source to the given detector. A more accurate version would be proportional to the volume of the intersection between the cubic voxel and the set of rays from the source to all points on the face of the given detector. None of these captures the imperfections of a real scanner. The set of sinogram values resulting from the mass at a given voxel tends to be more blurred than any of the above versions. The use of the PSF in the case of a linear projection model $F(x)=Ax$ includes two forms, (a) augmentation of the model deriving $A_{ij}$ from the cubic voxel and ideal point-to-point X-ray with blurring due to system non-idealities and (b) retrieving of $A_{ij}$ values from arrays describing the entire effect of voxel j on measurement i. Case (a) represents a use of the term "point spread function" in the sinogram in the sense most often applied in the literature, while case (b) uses the word "point" more broadly to represent a single voxel's center projected to a point on the sinogram, with "point spread function" in this case being the form of the total response in the sinogram domain to a single voxel, shifted to the location of said projected point. These two cases are treated separately. Also described is a process of estimating the form of the PSF prior to its application.

With reference to (a) above (i.e., using the PSF as a supplement to traditional solid voxel modeling), computing $A_{ij}$ from the intersection between a ray and a cubic voxel depends on the assumption that radiation is emitted from a single point, and that detector measurements are captured over negligible surface areas. However, the aperture size in a CT scanner must, in order to release adequate radiation, have area, just as the receiving detector absorbs radiation from a set of rays terminating at all points across the detector surface. The deviation, supplemental to random noise, between the ideal and actual contribution of pixel j to measurement i can be approximated as a convolution of the set of $A_{ij}$, as represented in the two-dimensional detector array indexed by i, with an array of values equivalent to a linear filter in two dimensions. Linear non-ideality of the solid voxel/linear ray system may be accommodated in the system model as this postprocessing of projection matrix values.

This linear operation on forward projections in Ax may be represented by a matrix B, with the more complete forward system model now captured in the product BA. The model of the sinogram data is then $y=BAx+n$, with n representing random noise. This BA model allows a number of practical implementations of the PSF enhancement. The simplest case consists of a simple filtering of Ax by a stationary linear filter. This single PSF is designed under the assumption that the blur of the system is independent of voxel position and orientation. The natural magnification of voxel projections as a function of distance from the source is included in the computation of Ax. Smoothing of forward projections is accomplished by filtering, either through direct convolution or fast Fourier transforms (FFTs). Exact implementation would require filtering forward projections before the computation of each iterative update in x, whether the update is made for a single voxel, as in iterative coordinate descent, or of the entire reconstruction, as in gradient descent methods. However, sufficient accuracy may be possible, even in coordinate-wise descent, with filtering only at the completion of updates of an entire plane or the entire three-dimensional volume of reconstruction.

Figure 3:
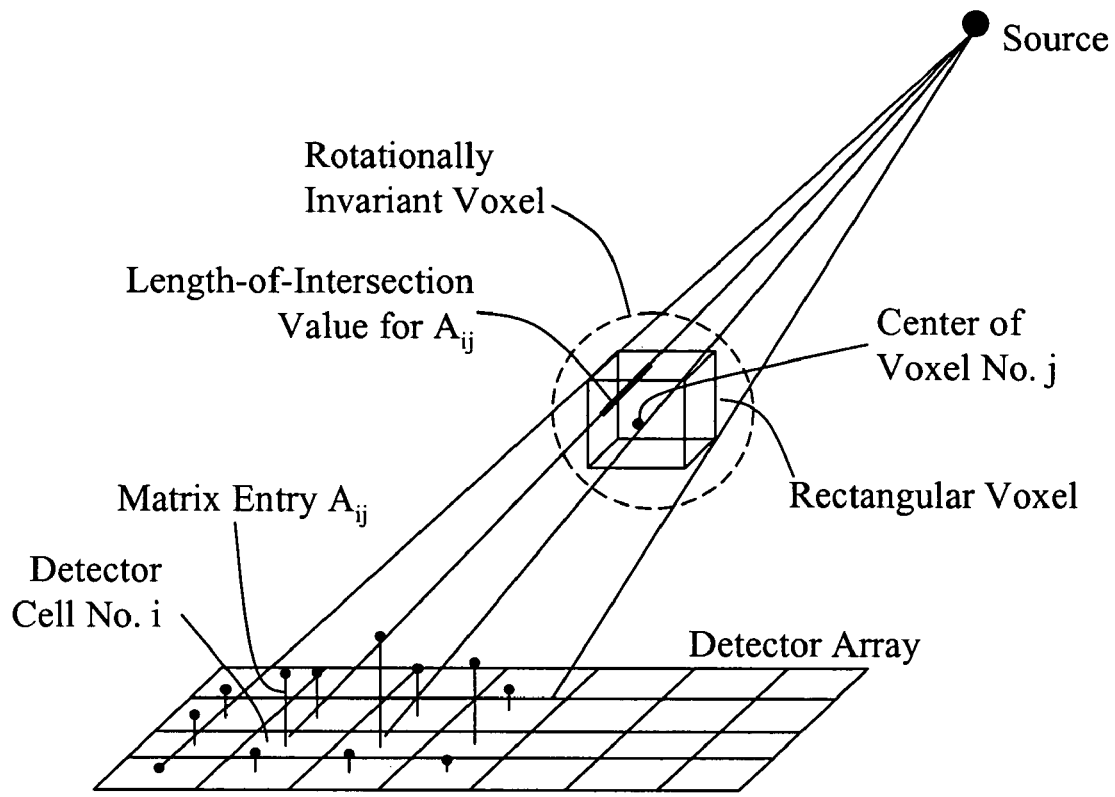
FIG. 3 illustrates a source, voxel, and detector geometry.

With respect to (b) above (i.e., using the PSF in a complete pixel-sinogram mapping), the simplest form of mapping from voxel into detector array includes casting a ray from the source through the center of a voxel and onto the detector plane, then attributing all contribution of the voxel to the detector in which the ray falls. In FIG. 3, this would be the detector with the largest illustrated value of $A_{ij}$. This is a discretization of the pure mapping of a point in image space to a point on the detector array, and is similar to a "perfect" PSF represented by an impulse, convolution with which changes nothing in a signal. Such a transformation uses only the computation of the location of the ray's intersection with the detector array, a relatively inexpensive task compared to methods depending directly on the shape and volume of the voxel in question. As in conventional signal processing, one may use a PSF to describe the transformation from the idealized point-to-point mapping to a realistic description of the CT detector array response to a single voxel. In this case, much more is demanded from the PSF model than in the scheme of (a). The possible contribution of a voxel to attenuation in multiple detectors must be appropriately modeled, giving this PSF a spatial support similar to the result of convolving the system's true physical PSF with the purely geometrically based solid voxel forward projection.

This second option (b) may involve more complexity in the PSF specification. The positive aspect of the trade-off is the potential for great computational savings. By storing a collection of high-resolution digital two-dimensional sinogram domain PSF profiles in memory and accessing the profile specified by such parameters as relative X-ray/voxel orientation difference and voxel/detector separation distance, one can retrieve the elements of BA as a table look-up. The addresses of values to extract from the array are determined by the distances, in the detector row and channel directions, between the projection point of the center of the voxel and the centers of nearby detector faces. The values of projection matrix entries shown in FIG. 3 could be retrieved by centering a complete, continuous-variable PSF at the point where the voxel center is projected onto the detector, then sampling the PSF at the centers of adjacent detector elements. The number of PSFs to be stored depends on the complexity of the modeled voxel. A cubic voxel requires a large amount of storage for PSFs because the shadow caused by the voxel's integral projection onto the detector array varies according to two angular variables. The greater the extent to which the system's true PSF blurs this profile, the weaker the dependence of the PSF array on orientation, and the smaller the number of separate PSF profiles which is stored. Significant storage can be saved by using spherically symmetric voxel models, also shown in FIG. 3, which eliminates dependence on orientation. In this case, a single PSF array may be used and simply scaled. As in the "solid voxel" option above, a scaling of distances into the PSF array depends on the voxel-detector distance.

As an option to (a) above, a computation of sinogram response to a single voxel may be made directly from the ideal model of voxel size and structure and geometric description of the CT scanner. Accurate description of the system's complete behavior in a closed mathematical form, though, is quite difficult. As herein described, two techniques are designed for determining PSFs based on the same underlying principle, comparison of sinogram data (y) to F(x) when x is known to accurately represent the actual object scanned.

The first PSF estimation approach employs computer simulation of the operation of the scanner to collect sinogram data y from a simply described object. For example, the scan of a single cube or sphere may be simulated. These sinogram data are then compared to F(x), with x as an accurate digital representation of the object scanned in simulation. Any limitations in the accuracy of the forward model F(x) are then attributed to the convolution of F(x) with the system's PSF, which is denoted as G in square matrix form. The form of G is then solved via minimization $$\hat{G} = \underset{G}{\operatorname{argmin}} D\{y, GF(x)\},$$

where D is a function penalizing differences between its two vector arguments in the sinogram space.

When D is the total squared distance metric, the common least-squares problem is encountered. When F is the linear transformation expressed as the matrix A, the operator G is identical to B above. A stationary convolution model reduces the number of unique coefficients to estimate to the size of the filter.

Reconstruction via option (b) above may demand a potentially greater number of parameters, since it cannot be represented by simple forward projection followed by sinogram processing. The above (b) requires the PSF coefficients used to be matched to each ij pair. Fortunately, these PSFs vary only in terms of the two angles of source-voxel orientation, and source-voxel distance, allowing dimension reduction of PSF storage. Simulation-based estimation of these PSF profiles at high resolution are taken from simulated scans of objects of the same form, though not necessarily the same size, as the unit voxels to be used in the reconstruction. In this case, the PSF's estimate is exactly the low-noise simulated forward projection of the voxel-shaped object onto a finely sampled detector plane. If the voxel is modeled as a rectangular solid, the PSF would appear as in FIG. 3, though with a resolution higher than the detector spacing, for the sake of interpolation for shifts between detector centers and voxel center projections.

A second PSF estimation technique involves physically scanning a real phantom of simple description, such as a cube, cylinder or sphere, in the scanner to be characterized. Computationally, the problem is identical to the above, with F(x) being the forward model to which the PSF is to be subsequently applied. The coefficients for the sinogram filtering modeled PSF are estimated as described above, matching actual scan data and a software forward projection of a discretized version of the exact, known object.

One technical effect of the herein described methods, apparatus, and software is an improvement in the accuracy of forward projection models in iterative CT X-ray image reconstruction by including a point spread function (PSF) in the model of the CT system.

While the invention has been described in terms of various specific embodiments, those skilled in the art will recognize that the invention can be practiced with modification within the spirit and scope of the claims.

What is claimed is:

1. A method of reconstructing an image, said method comprising performing an iterative CT X-ray image reconstruction using a model including a point spread function (PSF) to reconstruct an image, wherein the PSF is applied to a transformation from the image to a sinogram during the iterative reconstruction.

2. A method in accordance with claim 1, wherein said performing an iterative image reconstruction comprises performing an iterative image reconstruction wherein sinogram data is modeled in accordance with y=Ax+n, where y represents measured sinogram values, x represents an image, n represents noise, and each column of a matrix A represents the PSF of a voxel in the sinogram domain.

3. A method in accordance with claim 1, wherein said performing an iterative image reconstruction comprises performing an iterative image reconstruction wherein sinogram data is modeled in accordance with y=BAx×n, where y represents measured sinogram values, x represents an image, n represents noise, A represents a solid voxel model, and B represents a linear operator.

4. A method in accordance with claim 1, wherein said performing an iterative image reconstruction comprises performing an iterative image reconstruction wherein sinogram data is modeled in accordance with y=BAx×n, where y represents measured sinogram values, x represents an image, n represents noise, A represents a solid voxel model, and B represents a stationary linear filter.

5. A method in accordance with claim 1, wherein said performing an iterative image reconstruction comprises calculating the PSF by a computer simulation of a scan of an object.

6. A method in accordance with claim 1, wherein said performing an iterative image reconstruction comprises calculating the PSF by a computer simulation of a scan of an object and solving $$\hat{G} = \underset{G}{\operatorname{argmin}} D\{y, GF(x)\},$$

where G is a linear operator, $\hat{G}$ is the value of G which achieves a minimum, y represents simulated sinogram data, F(x) is a forward model, x is a digital representation of the object, and D is a function penalizing differences between its two vector arguments.

7. A method in accordance with claim 1, wherein said performing an iterative image reconstruction comprises calculating the PSF by scanning an object and solving $$\hat{G} = \underset{G}{\operatorname{argmin}} D\{y, GF(x)\}$$

where G is a linear operator, $\hat{G}$ is the value of G which achieves a minimum, y represents sinogram data of the object, F(x) is a forward model, x is a digital representation of the object, and D is a function penalizing differences between its two vector arguments.

8. A method in accordance with claim 1, wherein said performing an iterative image reconstruction comprises calculating the PSF by computer simulating an object having the same shape as a unit voxel of the reconstruction.

9. A method in accordance with claim 1, wherein said performing an iterative image reconstruction comprises calculating the PSF by computer simulation of an object having the same shape and size as a unit voxel of the reconstruction.

10. A method in accordance with claim 1, wherein said performing an iterative image reconstruction comprises calculating the PSF by computer simulation of an object having a shape the same as a unit voxel of the reconstruction and with a PSF resolution higher than the resolution of a detector spacing.

11. A method in accordance with claim 1, wherein said performing an iterative image reconstruction comprises calculating the PSF by computer simulation of an object having a shape the same as a rectangular solid shaped unit voxel of the reconstruction and with a PSF resolution higher than the resolution of a detector spacing.

12. A method in accordance with claim 1, wherein said performing an iterative image reconstruction comprises calculating the PSF by computer simulation of an object having a shape the same as a unit voxel of the reconstruction wherein the unit voxel is spherical.

13. A Computed Tomography (CT) System comprising:
an X-ray source;
a radiation detector; and
a computer coupled to said X-ray source and said radiation detector, said computer configured to perform an iterative X-ray image reconstruction using a model function including a point spread function (PSF) to reconstruct an image, wherein the PSF is applied to a transformation from the image to a sinogram during the iterative reconstruction.

14. A system in accordance with claim 13 wherein said computer is further configured to perform an iterative image reconstruction wherein sinogram data is modeled in accordance with y=BAx+n, where y represents measured sinogram values, x represents an image, n represents noise, A represents a solid voxel model, and B represents a stationary linear filter.

15. A system in accordance with claim 13 wherein said computer is further configured to perform an iterative image reconstruction wherein sinogram data is modeled in accordance with y=Ax×n, where y represents measured sinogram values, x represents an image, n represents noise, and each column of a matrix A represents the PSF of a voxel in the sinogram domain.

16. A system in accordance with claim 13 wherein said computer further configured to calculate the PSF by simulation of a scan of an object.

17. A system in accordance with claim 13 wherein said computer further configured to calculate the PSF by simulation of a scan of an object and solving $$\hat{G} = \underset{G}{\mathrm{argmin}}\, D\{y, GF(x)\},$$

where $\hat{G}$ is the value of G which achieves a minimum, y represents simulated sinogram data, F(x) is a forward model, x is a digital representation of the object, and D is a function penalizing differences between its two vector arguments.

18. A system in accordance with claim 17 wherein said computer further configured to simulate a scan of an object having a shape the same as a unit voxel of the reconstruction.

19. A system in accordance with claim 13 wherein said computer further configured to receive data regarding a scan of an object and calculate the PSF by solving $$\hat{G} = \underset{G}{\mathrm{argmin}}\, D\{y, GF(x)\},$$

where $\hat{G}$ is the value of G which achieves a minimum, y represents sinogram data of the object, F(x) is a forward model, x is a digital representation of the object, and D is a function penalizing differences between its two vector arguments.

20. A computer readable medium encoded with a program configured to instruct a computer to:
generate a model function including a point spread function (PSF); and
reconstruct an X-ray CT image by applying the PSF to a transformation from the image to a sinogram during an iterative reconstruction.

21. A medium in accordance with claim 20 where said program further configured to instruct the computer to receive data regarding a scan of an object and calculate the PSF by solving $$\hat{G} = \underset{G}{\mathrm{argmin}}\, D\{y, GF(x)\},$$

where $\hat{G}$ is the value of G which achieves a minimum, y represents sinogram data of the object, F(x) is a forward model, x is a digital representation of the object, and D is a function penalizing differences between its two vector arguments.

22. A medium in accordance with claim 20 where said program further configured to instruct the computer to calculate the PSF by simulation of a scan of an object and solving $$\hat{G} = \underset{G}{\mathrm{argmin}}\, D\{y, GF(x)\},$$

where $\hat{G}$ is the value of G which achieves a minimum, y represents simulated sinogram data, F(x) is a forward model, x is a digital representation of the object, and D is a function penalizing differences between its two vector arguments.

23. A medium in accordance with claim 20 where said program further configured to instruct the computer to perform an iterative image reconstruction wherein sinogram data is modeled in accordance with y=Ax×n, where y represents measured sinogram values, x represents an image, n represents noise, and each column of a matrix A represents the PSF of a voxel in the sinogram domain.

* * * * *